US005709695A

United States Patent [19]

Northrup, III

[11] Patent Number: 5,709,695
[45] Date of Patent: Jan. 20, 1998

[54] APPARATUS FOR REDUCING THE CIRCUMFERENCE OF A VASCULAR STRUCTURE

[75] Inventor: William F. Northrup, III, Edina, Minn.

[73] Assignee: Segmed, Inc., Edina, Minn.

[21] Appl. No.: 705,179

[22] Filed: Aug. 29, 1996

Related U.S. Application Data

[62] Division of Ser. No. 288,124, Aug. 10, 1994, Pat. No. 5,593,424.

[51] Int. Cl.$^6$ .................................................. A61B 17/00
[52] U.S. Cl. .................................... 606/148; 606/232
[58] Field of Search .............................. 606/232, 233, 606/148, 1; 623/2; 128/898

[56] References Cited

U.S. PATENT DOCUMENTS

| | | | |
|---|---|---|---|
| 4,164,046 | 8/1979 | Cooley | 623/2 |
| 4,217,665 | 8/1980 | Bex et al. . | |
| 4,275,736 | 6/1981 | Chodorow et al. . | |
| 4,489,446 | 12/1984 | Reed . | |
| 4,637,380 | 1/1987 | Orejola . | |
| 4,676,245 | 6/1987 | Fukuda . | |
| 4,823,794 | 4/1989 | Pierce . | |
| 4,917,698 | 4/1990 | Carpentier et al. . | |
| 5,011,481 | 4/1991 | Myers et al. . | |
| 5,041,130 | 8/1991 | Cosgrove et al. . | |
| 5,061,277 | 10/1991 | Carpentier et al. . | |
| 5,064,431 | 11/1991 | Gilbertson et al. . | |
| 5,089,008 | 2/1992 | Chen . | |
| 5,104,407 | 4/1992 | Lam et al. . | |
| 5,163,943 | 11/1992 | Mohiuddin et al. . | |
| 5,201,880 | 4/1993 | Wright et al. . | |
| 5,219,359 | 6/1993 | McQuilkin et al. . | |
| 5,258,021 | 11/1993 | Duran . | |
| 5,263,973 | 11/1993 | Cook . | |
| 5,306,301 | 4/1994 | Graf et al. . | |
| 5,366,480 | 11/1994 | Corriveau et al. . | |
| 5,468,242 | 11/1995 | Reisberg . | |
| 5,549,631 | 8/1996 | Bonutti . | |

FOREIGN PATENT DOCUMENTS 1335260  9/1987  U.S.S.R. .

OTHER PUBLICATIONS

Product Pamphlet "Prosthetic Rings and Accessories for Tricuspid and Mitral Valvuloplasty" produced by American Edwards Laboratories, in Dec., 1985.

Van Rijk—Zwikker, et al., "Mitral Valve Anatomy and Morphology: Relevance to Mitral Valve Replacement and Valve Reconstruction," J. Card. Surg., 1994; 9 (Suppl): 255–261.

Primary Examiner—Jeffrey A. Schmidt
Attorney, Agent, or Firm—Patterson & Keough, P.A.

[57] ABSTRACT

An apparatus and method for reducing the circumference of a vascular structure comprising the steps of providing a plurality of sutures and a plurality of discrete suture support segments of a biocompatible, inert material, each suture support segment having at least two suture holes spaced a predetermined distance (D) apart; individually suturing each discrete suture support segment to the vascular structure with one of the plurality of sutures by effecting a horizontal mattress (U-shaped) suture along the vascular structure through a length of tissue of the vascular structure such that the length (D') of tissue sutured is greater than distance (D); and tightening and tying off the suture, whereby each sutured suture support segment creates an imbrication in the vascular structure, thereby reducing the circumference thereof. A biocompatible, inert stabilizing material may optionally be affixed over the suture support segments and the vascular structure after prior to tying off the suture to stabilize the interval between the suture support segments and eliminate direct exposure of the segmented apparatus to blood.

23 Claims, 3 Drawing Sheets

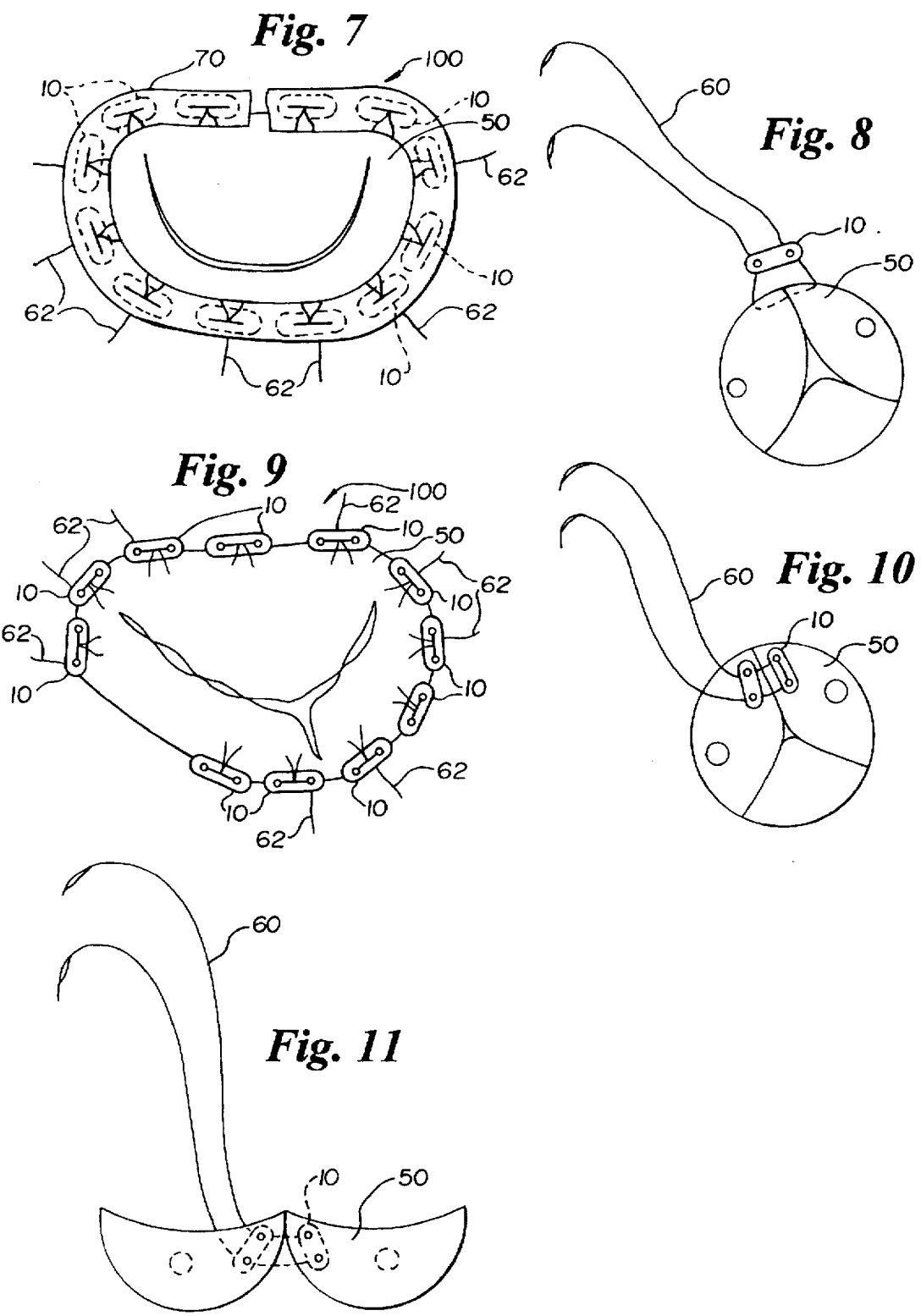

APPARATUS FOR REDUCING THE CIRCUMFERENCE OF A VASCULAR STRUCTURE

This is a Division of application Ser. No. 08/288,124 filed Aug. 10, 1994, now U.S. Pat. No. 5,593,424.

BACKGROUND OF THE INVENTION

The present invention relates generally to an apparatus and method for reducing the circumference of a vessel, and more particularly to an apparatus and method for reducing the circumference of vascular structures, including cardiac valves.

All artificial or prosthetic heart valves, whether mechanical or bioprosthesis, although greatly improving the condition of the patient, have some serious drawbacks; namely thrombogenicity (tendency towards thrombus formation and subsequent detachment with embolization), and limited durability secondary to tissue structure failure.

Other complications such as noise, interference with hemodynamics, especially in smaller sizes, hemolysis (destruction of blood elements), risk of thromboembolism in all patients who receive mechanical valves, endocarditis (valve infection) and dehiscence of the valve also occur. Because of the risk of embolism, the majority of patients who receive artificial heart valves need to take anticoagulative medication for life with the concomitant risk of hemorrhage and necessary change in life style.

Different and more recent developments in the field of cardiac surgery included attempts to surgically repair diseased vascular tissue, in particular, heart valves. A variety of surgical maneuvers or procedures have been used for this purpose. This type of reconstructive surgery has been shown to be superior to valve replacement in many respects.

Reconstructive surgery, however, is generally more difficult to perform than replacement and is not always possible in every patient. Among the variety of reconstructive maneuvers, valve annuloplasty is the most frequently performed in the tricuspid and mitral valves. Valve annuloplasty is an operation which selectively reduces the size of the valve annulus. For this purpose, a number of prosthetic rings have been developed for the atrioventricular valves. One such well known commercially available ring is the Carpentier (distributed by American Edwards Laboratories) ring.

The Carpentier method of valvuloplasty employing the Carpentier ring is disclosed in the product pamphlet "Prosthetic Rings and Accessories for Tricuspid and Mitral Valvuloplasty", produced by American Edwards Laboratories in December, 1985.

Carpentier et al., U.S. Pat. No. 5,061,277 relates to a flexible cardiac valvular support prosthesis which is generally ring shaped and has a first length which is flexible and a second length which is less flexible than the first length, so the support may shape the annulus while the first length of the support in place in a heart valve annulus allows contraction thereof.

Carpentier et al., U.S. Pat. No. 4,917,698 relates to a multi-segmented annuloplasty ring prosthesis for use in the surgical correction of a deformed heart valve, which provides a substantially circular body comprising in part segments joined together by flexible joints, the body being shaped in proportion to the annulus of a heart valve.

Duran, U.S. Pat. No. 5,258,021 relates to a Sigmoid Valve Annuloplasty Ring in a scalloped shape having three sinusoidal struts to adapt to the anatomical shape of the annulus of the human sigmoid valves. The ring is made of a biocompatible material covered with a biocompatible cloth.

Lam et al., U.S. Pat. No. 5,104,407 relates to a selectively flexible annuloplasty ring for suturing to the annulus of a heart valve, the annular ring comprising a partially flexible length and a partially rigid length. The ring is covered in a suturable material.

Wright et al., U.S. Pat. No. 5,201,880 relates to Mitral and Tricuspid Annuloplasty Rings having a unitary construction with internal drawstrings and a semi-flexible stiffener in the anterior segment.

Cosgrove et al., U.S. Pat. No. 5,041,130 relates to an assembly for holding a substantially flexible lenticular shaped annuloplasty ring in a position for suturing about a valve annulus. The unitary annuloplasty ring contemplated therein is substantially flexible, and is partially circumferential, encompassing only the posterior mitral annulus.

Reed, U.S. Pat. No. 4,489,446 relates to an adjustable heart valve prosthesis with unitary construction including a dynamic stiffener element.

Gilbertson et al., U.S. Pat. No. 5,064,431 relates to an annuloplasty ring of tubular construction including drawstrings selectively adjustable to adjust the annulus to a desired shape.

Myers et al. U.S. Pat. No. 5,011,481 relates to a holder for an annuloplasty ring for use in implantation.

Commercially available annuloplasty rings have several drawbacks. First, they are expensive. Second, unless they are either rigid or sutured to the tissue annulus while still attached to a rigid holder, they may not provide a precise, predictable reproducible annuloplasty because of the unpredictable degree of longitudinal shortening along the circumference of the sutures within the confines of each mattress suture used to secure the ring to the tissue annulus. Each suture is necessarily tied with variable and unpredictable degrees of tension by the operating surgeon.

Third, most mitral rings are completely circumferential committing the operating surgeon to placing sutures in the anterior annulus where dilatation rarely occurs and where a tissue tear from inexact suture placement can produce significant mitral regurgitation. Fourth, a rigid mitral ring, because it is preshaped to an oval configuration, must be precisely placed or an unsatisfactory annuloplasty may result. Fifth, a rigid tricuspid ring can dehisce if not made to conform to the slightly spiral, nonplanar shape of the tissue annulus. Sixth, any rigid ring prevents the normal flexibility of the tissue annulus of the atrioventricular valve during ventricular contraction.

A need exists for an apparatus and method which provides a customized annuloplasty, tailored to the needs of specific pathophysiological situations, including but not limited to a limited annuloplasty or commissuroplasty of any valve annulus, a subtotal annuloplasty of any valve or a complete annuloplasty of any valve annulus. A need also exists for an apparatus and method which allows the repaired vascular structure to retain its flexibility in all planes while preventing further dilatation, or circumferential lengthening of the tissue annulus or vascular structure.

It has been found that to achieve such objects, a commercially available annuloplasty ring is not necessary. Such objects may be effected through use and implantation of an annuloplasty device comprising a series of discrete suture support segments.

SUMMARY OF THE INVENTION

The basic and general object of the present invention is to provide a method and apparatus that maintains the normal shape of a vessel or induces the vessel to regain its normal shape.

More specifically, when performing a valve annuloplasty, the object of the present invention is to implant a device which reduces the circumference of a diseased cardiac valve annulus or vascular structure to the desired size. Specifically, repositioning of displaced and incompetent valvular cusps and commissures or reduction and remodeling of annular or vascular dilatation by precisely defined plications (tucks or folds) at specified points is effected.

The inventive method of reducing the circumference of a vascular structure having an upper portion and a lower portion, said upper and lower portions of the vascular structure defining an upper circumference and a lower circumference of said vascular structure, comprises the steps of:

a) providing a plurality of discrete suture support segments of a biocompatible inert material, each suture support segment further comprising an upper surface, a lower surface, opposite sides, a proximal end, a distal end and at least two suture holes extending from the upper surface to the lower surface thereof and being spaced a predetermined distance (D) apart;

b) providing a suture;

c) individually suturing each suture support segment to the vascular structure whose circumference is to be reduced by means of a horizontal mattress (U-shaped) suture along the vascular structure through a length of tissue of the vascular structure such that the length (D') of tissue sutured is greater than distance (D); and d) tightening and tying off the suture, whereby each sutured segment creates an imbrication in the vascular structure, thereby reducing the circumference thereof by an amount equal to (D')-(D).

Alternatively, the method may comprise the further step of affixing a biocompatible, inert stabilizing material over the suture support segments and the vascular structure by means of horizontal mattress sutures through each suture support segment and through the tissue of the vascular structure, said stabilizing material being of predetermined dimensions sufficient to cover the suture support segments affixed to the vascular structure, thereby stabilizing the interval between the suture support segments in order to prevent further lengthening of the vascular structure, and eliminating direct exposure of the suture support segments to blood.

BRIEF DESCRIPTION OF THE FIGURES

FIG. 7 is a top view of a complete mitral valve annuloplasty according to the present invention;

FIG. 8 is a top view of an aortic valve commissuroplasty (localized annuloplasty) according to the present invention;

FIG. 9 is a top view of a tricuspid valve annuloplasty according to the present invention;

FIGS. 10 is a top view of a commissural annuloplasty of a semilunar valve;

FIG. 11 is a side view of a commissural annuloplasty of a semilunar valve;

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
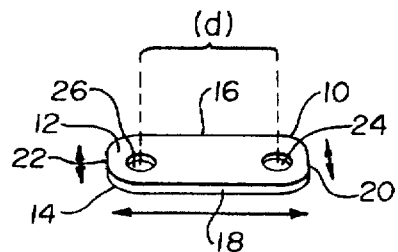
FIG. 1 is a perspective view of a suture support segment of the present invention.

The present invention provides an apparatus and method for reducing the circumference of a vascular structure. The present invention also provides an apparatus and method for permanently reconstructing a vascular structure to a normal configuration, to restore its original form and function. The apparatus comprises a plurality of suture support segments like that shown generally at 10 in FIG. 1, sutured to a vascular structure. A plurality of suture support segments is shown in place generally at 100 in FIG. 4. As shown in FIG. 1, each individual suture support segment 10 comprises an upper surface 12, a lower surface 14, opposite sides 16, 18, a proximal end 20, and a distal end 22. Each suture support segment 10 has at least two suture holes. The embodiment shown at FIG. 1 has a first suture hole 24 and a second suture hole 26 extending from upper surface 12 to lower surface 14, spaced a predetermined distance (D) apart. Suture holes 24, 26 should be large enough to accommodate a 2-0 suture and swedged-on needle. In addition, suture holes 24, 26 should be smooth in order to prevent suture fraying or cutting when suture 60 is tied. The distance (D) between suture holes 24, 26 may be varied, although an interval of 5 mm (±3 mm) from center to center of holes 24, 26 is suitable.

Although any suitable suture may be used, the most preferred as shown in the figures has a swedged-on surgical needle at each end thereof. Alternatively, a single needle suture may be used.

Suture support segment 10 may be made of any suitable material which is biocompatible with blood and tissue, inert, non-corrosive and non-thrombogenic. As a practical matter, the material of which suture support segment 10 is made should be a substance already approved for intra-vascular use by the FDA such as titanium. Suture support segment 10 must be rigid or semi-rigid in the longitudinal dimension, and must not be deformable, so that it does not buckle when suture 60 is tied.

Although suture support segment 10 may be of any suitable shape, the spatulated shape shown in FIG. 1 is quite effective. The minimum dimension from outside edge of suture hole to the end of suture support segment 10 in order to minimize the chance of abutment or overlap of adjacent suture support segments is about 1 mm. The minimum width to minimize mass but not to allow cutting into tissue is between about 2 mm-4 mm. The minimum thickness to reduce mass but avoid buckling of suture support segment 10 is about 1 mm.

Figure 2:
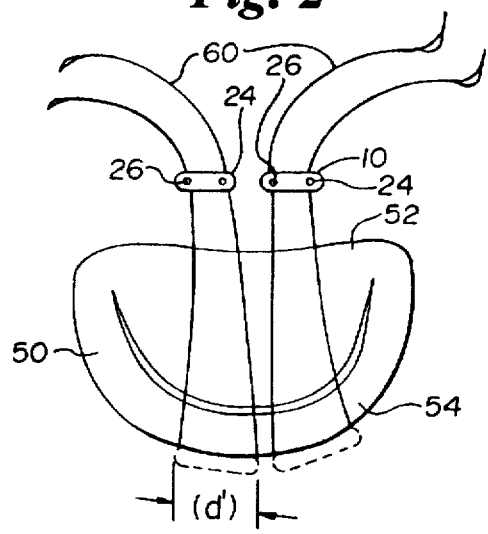
FIG. 2 shows a top view of a vascular structure (i.e., mitral valve) upon which suture support segments for reducing the circumference of a vascular structure according to the present invention are being sutured.

The method of reducing the circumference of vascular structure is shown at FIGS. 2-6. As shown at FIG. 2, vascular structure 50 has an upper portion 52 and a lower portion 54, said upper and lower portions 52, 54 defining an upper circumference and a lower circumference of vascular structure 50.

Figure 3:
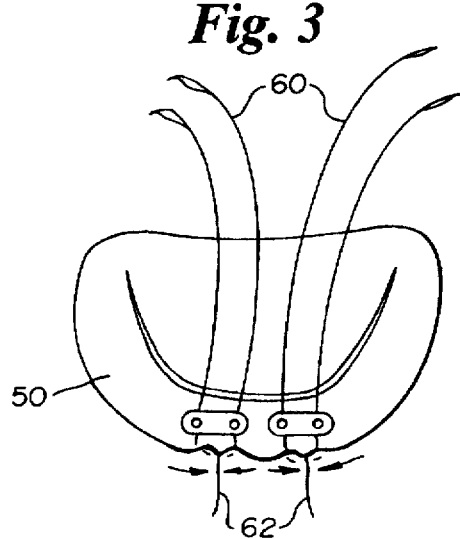
FIG. 3 shows a top view as in FIG. 1 wherein the tissue of the vascular structure has been imbricated according to the present invention.

Apparatus 100 comprising a plurality of suture support segments 10. Suture support segments 10 are individually affixed to vascular structure 50 whose circumference is to be reduced, by means of a horizontal mattress (U-shaped) suture 60 along vascular structure 50 through a length of tissue of vascular structure 50. Referring to FIG. 2, the suture 60 traverses a longer distance along vascular structure 50 than the distance (D) between suture holes 24, 26 of suture support segment 10. Specifically, the length or distance (D') between the entry and exit of suture 60 is greater than distance (D) between suture holes 24, 26 of suture support segment 10. As shown in FIGS. 2 and 3, both ends of suture 60 are brought up through suture holes 24, 26 of suture support segment 10. The length (D') of tissue of vascular structure 50 sutured is greater than distance (D), whereby each sutured segment 10 creates an imbrication, or tuck 62, in vascular structure 50, thereby reducing the circumference thereof.

Sutures 60, when tied, will reduce the circumference of a vascular structure by an amount equal to (D')-(D), the difference between the length (D') each individual mattress suture 60 travels in the tissue of vascular structure 50 and the distance (D) between the 2 suture holes 24, 26 in the individual suture support segment 10. In other words, vascular structure 50 is imbricated underneath suture support segment 10, within the individual mattress suture, by a precise amount depending on the linear distance (D') along the tissue of vascular structure 50 which the individual suture 60 travels.

Figure 4:
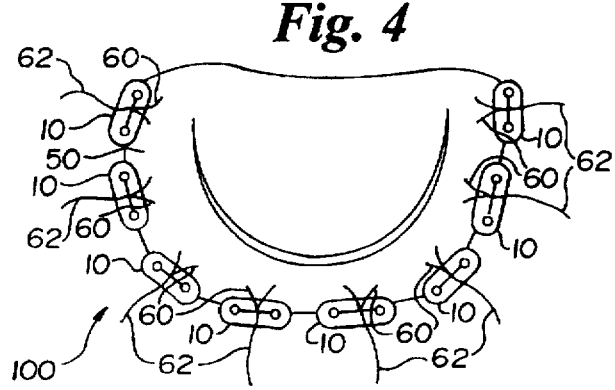
FIG. 4 is a top view as in FIG. 1 showing the suture support segments in place on a vascular structure (i.e., mitral valve) whose circumference is thereby reduced according to the present invention.

A plurality of suture support segments 10 in place is shown at FIG. 4.

Figure 5:
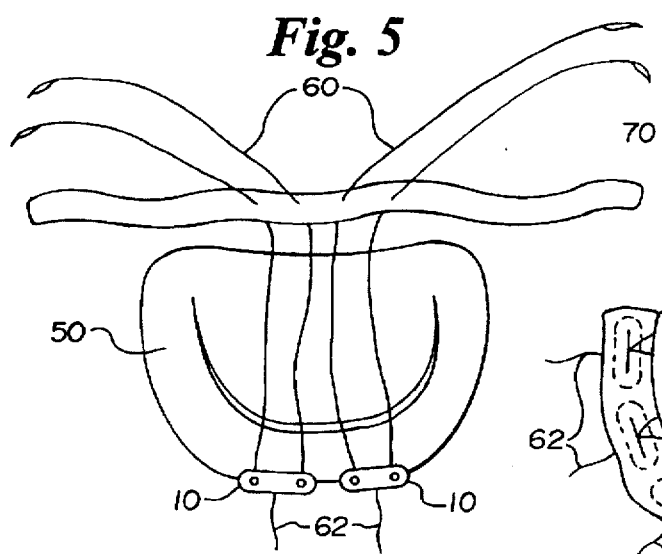
FIG. 5 is a top view as in FIG. 1 showing optional fixation of the stabilizing material over the suture support segments.

Referring to FIG. 5, a biocompatible, inert stabilizing material 70 may optionally be provided. As shown, stabilizing material 70 is also affixed over the segmented apparatus and the vascular structure by means of horizontal mattress sutures 60 through each segment and through the tissue of vascular structure 50. Stabilizing material 70 may be affixed to vascular structure 50 by means of the same sutures 60 used to affix segments 10 thereto. Both ends of suture 60 are brought up through stabilizing material 70 prior to tying of suture 60.

Alternatively, the stabilizing material and suture support segment may be sutured to vascular structure 50 with one continuous suture using a single needle. The mattress suture would be effected by passing the needle and suture first through the stabilizing material from an entry point in the upper surface thereof through the lower surface thereof, then through a suture hole in the suture support segment, suturing the length of tissue of the vascular structure, passing the suture through a second suture hole in the suture support segment, passing the suture through the stabilizing material from the lower surface thereof and out an exit point in the upper surface thereof. The suture would then be tightened and tied off such that the suture knot formed would sit on the upper surface of the stabilizing material. Alternatively, a running mattress suture would be possible by tying a single suture to itself or to an additional suture or by repeating the course of the running mattress suture in reverse.

Stabilizing material 70 is of predetermined dimensions sufficient to cover apparatus 100 affixed to vascular structure 50, and may actually be another layer of tissue such as autologous, homologous or heterologous pericardium, or alternatively may be made of any suitable fabric, such as dacron.

Figure 6:
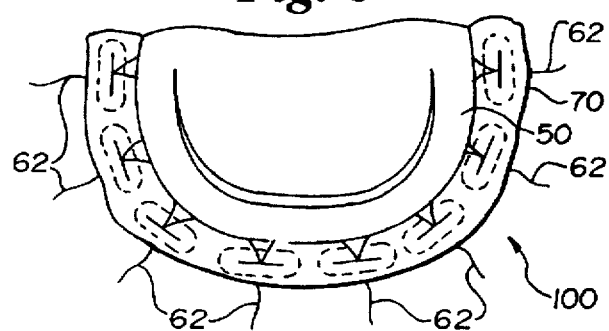
FIG. 6 is a top view as in FIG. 1 showing the suture support segments and stabilizing material in place.

Stabilizing material 70, shown in place in FIG. 6, stabilizes the interval between sutures 60, preventing further dilatation or circumferential lengthening of the tissue annulus or vascular structure between sutures. The stabilizing material 70 also eliminates direct exposure of the segmented apparatus 100 to blood.

The practice of the present invention achieves several objectives and advantages. The objectives and advantages are as follows.

The segmented apparatus of the present invention is much less expensive to produce than commercial annuloplasty rings, as it comprises discrete suture support segments which are economical to produce.

The apparatus and method allows precise imbrication within each mattress suture supported by suture support segments. This is not possible with any annuloplasty device which is deformable in a longitudinal direction unless the device is attached to a rigid holder while the sutures are tied. The present apparatus and method allows for an absolutely precise, predictable and reproducible annuloplasty.

Figure 12:
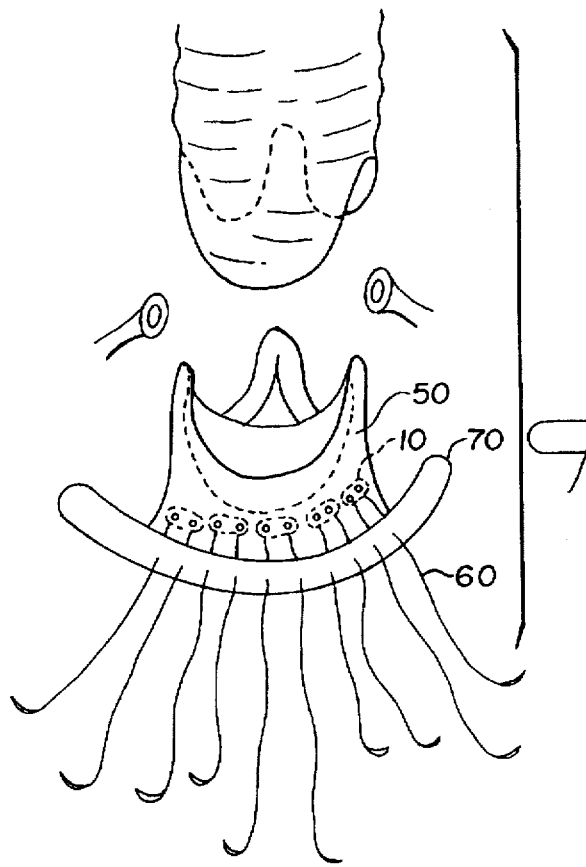
FIGS. 12 and 13 are views of a stabilizing annuloplasty of the aortic valve annulus in an aortic valve-sparing root replacement with a dacron conduit, FIG. 12 being a side view of stabilization from the outside of the reconstructed aortic root and FIG. 13 being a view of an opened aorta showing the stabilization from the inside of the reconstructed aortic root.
Figure 13:
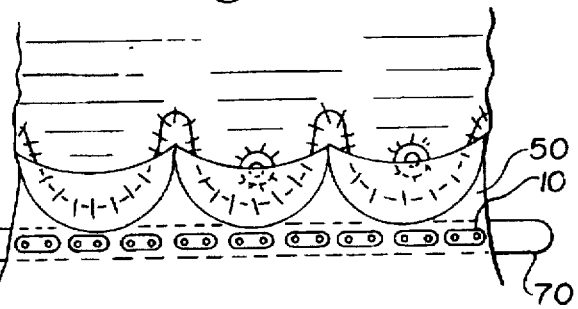
Figure 14:
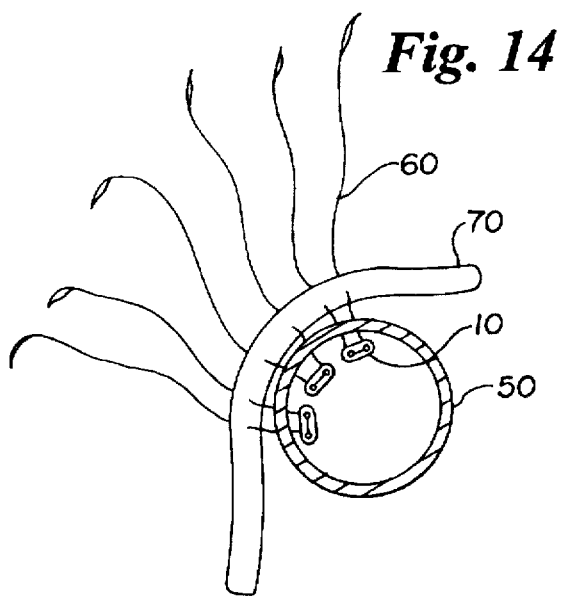
FIG. 14 is a top sectional cut-away view of a left ventricular outflow tract showing the level of the stabilizing annuloplasty immediately below the aortic valve (as shown in FIGS. 12 and 13).

The inventive apparatus and method provide construction of a customized annuloplasty, not possible with commercial annuloplasty rings. A limited annuloplasty or commissuroplasty of any valve annulus, as shown in FIGS. 8, 10 and 11 can be performed, as can a posterior mitral valve annuloplasty as shown in FIGS. 4 and 6, as well as a subtotal annuloplasty of any valve such as the tricuspid valve, as shown in FIG. 9, or a complete annuloplasty of any valve annulus as shown in FIG. 7. FIGS. 10 and 11 show a commissural annuloplasty of a semilunar valve. FIGS. 12, 13 and 14 show a stabilizing annuloplasty of the aortic valve annulus.

The discrete suture support segments allow flexibility of the annulus or vascular structure in all planes, analogous in principle to a chain-link fence, although the links are separate. The resulting annuloplasty is more physiologic than with a rigid ring since it is flexible in all planes. In the case of the mitral and tricuspid valve annulus, systolic contraction is still possible.

The present invention provides not only an annuloplasty device which is not only less expensive than commercially available annuloplasty rings, but also a more precise, predictable reproducible annuloplasty than is provided by any flexible ring not attached to a rigid holder while the sutures are tied. The discrete suture support segments make it possible to reduce the circumference of the valve annulus by a specific length. A customized annuloplasty, including but not limited to a limited annuloplasty or commissuroplasty of any valve annulus, a subtotal annuloplasty of any valve or a complete annuloplasty of any valve annulus may thereby be provided.

Repair of a vascular structure with the present apparatus and method allows the repaired vascular structure to retain its flexibility in all planes, and further minimizes the possibility of dehiscence of the vascular structure, and the possibility of further dilatation, or circumferential lengthening of the vascular structure. Further, the possibility of failure of the present apparatus when in place at the tissue annulus is lessened by providing discrete suture support segments. Conversely, a rigid, unitary annuloplasty ring when implanted will by definition resist any physiological motion of the tissue annulus either downward (away from the lower surface of the ring) or inward (toward the orifice of the ring), and may therefore come out of its implanted site.

In addition, the need for temporary anticoagulation recommended with commercial annuloplasty rings is probably unnecessary with the present invention, especially if the segmented apparatus is covered with a stabilizing material such as pericardium, as no thrombogenic surfaces are exposed to the blood except for suture knots.

Suture knots are less likely to come untied when used in conjunction with a stabilizing material which is significantly deformable in a longitudinal direction, such as pericardium, since individual sutures can be tied firmly with uniform maximal tension against the non-deformable suture support segment without any possibility of additional longitudinal shortening of the tissue annulus due to excessive tension during knot-tying.

When the apparatus and method of the present invention is used in infants and growing children without the stabilizing material, the potential for growth of a vascular structure or cardiac valve annulus between the suture support segments is retained.

When used to perform a commissural annuloplasty of a semilunar valve, as shown in FIGS. 10 and 11, and the suture support segments are vertically oriented within the sinus on either side of the commissure just short of the leaflet hinge, no reduction in leaflet height occurs when the suture is tied. Such leaflet height reduction at the commissures could occur if the buttressing material were deformable (e.g. teflon felt pledget).

A "stabilizing" annuloplasty of the aortic valve annulus could be accomplished in operations wherein a dilated aortic root is replaced with a dacron conduit and the aortic valve is spared (e.g., Yacoub and David) particularly if the conduit is used to create "pseudo-sinuses" and does not engage the actual aortic valve annulus with sutures (FIGS. 12, 13). In such cases the suture support segments could be placed on the endocardial surface of the left ventricular outflow tract in a single horizontal plane immediately below the lowest points of the scalloped aortic valve sinuses avoiding contact with the leaflet hinge. The stabilizing material could then be placed on the epicardial surface (FIG. 14).

Although the present invention is particularly suited for reducing the circumference of vascular structures such as cardiac valves as indicated hereinabove, the apparatus and method may be applied to reduce the circumference of any valve, vessel or lumen in the body, including those in the digestive, genito-urinary, circulatory or respiratory systems. By the method described hereinabove, a plurality of suture support segments are sutured around a predetermined portion of the circumference of the structure, for example an intestinal lumen.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An anatomical structure circumference reduction apparatus for precisely reducing the circumference of an anatomical structure, the apparatus comprising:

a plurality of substantially rigid discrete support segments for disposition at least partially circumferentially about the anatomical structure to form a line of discrete support segments;

each segment consisting of opposite sides, a proximal end, a distal end, and structure defining only two suture apertures, the two suture apertures being constructed to receive and support suture material for attaching each segment with respect to the anatomical structure at a precise location, the suture apertures extending from a top surface of each segment to a bottom surface of each segment, the top surface and the bottom surface of each segment each being substantially planar, the line of segments being disposed and the suture apertures being spaced such that suture material passing through the suture apertures reduces the circumference of the anatomical structure by a precise amount along the line of segments.

2. The anatomical structure circumference reduction apparatus of claim 1, wherein the line of segments substantially prevents circumferential lengthening of the anatomical structure along the line of segments.

3. The anatomical structure circumference reduction apparatus of claim 1, wherein the line of segments is disposed for creating anatomical structure plication regions alternating with anatomical structure non-plication regions.

4. The anatomical structure circumference reduction apparatus of claim 1, further comprising stabilizing material for covering the line of segments to stabilize the line of segments and to substantially prevent contact of the line of segments with blood.

5. The anatomical structure circumference reduction apparatus of claim 1, wherein at least one segment includes a surface for supporting a layer of tissue to cover and stabilize the line of segments.

6. The anatomical structure circumference reduction apparatus of claim 1, wherein the line of segments is substantially curved.

7. The anatomical structure circumference reduction apparatus of claim 6, wherein the line of segments forms a partial ring shape.

8. The anatomical structure circumference reduction apparatus of claim 6, wherein the line of segments forms a substantially complete ring shape.

9. The anatomical structure circumference reduction apparatus of claim 1, wherein the line of segments is constructed such that sutures passing through the segments into a vascular structure plicate the vascular structure.

10. The anatomical structure circumference reduction apparatus of claim 9, wherein the line of segments is constructed to plicate the circumference of a valve annulus.

11. The apparatus of claim 1, wherein the top and bottom surfaces of each of the segments are free for direct exposure to material for covering the line of segments.

12. A vascular structure circumference reduction apparatus for precisely reducing the circumference of a vascular structure, the apparatus comprising:

circumference reduction means for creating a series of plication regions in the vascular structure, the circumference reduction means comprising a plurality of substantially rigid discrete support segments for disposition at least partially circumferentially about the vascular structure to form a line of discrete support segments, each plication region in the series of plication regions being disposed beneath each segment, and to reduce the circumference of the vascular structure along the circumference reduction means by a precise amount;

each segment of the circumference reduction means consisting of structure including opposite sides, a proximal end, a distal end, and only two aperture means for receiving and supporting suture means for attaching each segment to the vascular structure at a precise location, the structure having substantially flat opposite surfaces through which the aperture means passes; and the circumference reduction means providing flexibility to follow the vascular structure while substantially preventing circumferential lengthening of the vascular structure.

13. The vascular structure circumference reduction apparatus of claim 12, further comprising stabilizing means for covering the line of segments for stabilizing the line of segments and substantially preventing contact of the line of segments with blood.

14. The vascular structure circumference reduction apparatus of claim 12, wherein the line of segments is substantially curved.

15. The vascular structure circumference reduction apparatus of claim 14, wherein the line of segments forms a ring shape.

16. The vascular structure circumference reduction apparatus of claim 12, wherein the line of segments is discontinuous to create anatomical structure plication regions alternating with anatomical structure non-plication regions.

17. An apparatus for reducing the circumference of a vascular structure, the apparatus comprising in combination a plurality of discrete suture support segments disposed in a line and a plurality of horizontal mattress (U-shaped) sutures, each suture support segment being made of a non-deformable, biocompatible, inert material and comprising a substantially flat upper surface, a substantially flat lower surface, opposite sides, a proximal end, a distal end and only two suture holes extending from the upper surface to the lower surface thereof, the suture holes being spaced a predetermined distance apart, each suture support segment being substantially rigid and substantially non-deformable in a longitudinal dimension defined by said opposite sides, and being constructed and arranged to be individually sutured with one of the plurality of sutures to a length of tissue of the vascular structure whose circumference is to be reduced along the line of segments, the suture holes being spaced such that the length of tissue sutured is greater than the predetermined distance between the holes and such that each sutured suture support segment creates an imbrication in the vascular structure when each suture is tightened and tied off, reducing the circumference of the vascular structure along the line of segments.

18. The apparatus of claim 17, wherein the suture holes of each suture support segment are substantially smooth and of a diameter which accommodates a 2-0 suture and a swedged-on suture needle.

19. The apparatus of claim 17, wherein the distance between centers of the suture holes is about 5± about 3 mm, further wherein each suture support segment has a width of about 2–4 mm.

20. The apparatus of claim 17, wherein each suture support segment has a thickness of about 1 mm.

21. An anatomical structure circumference reduction apparatus kit for use in precisely reducing the circumference of an anatomical structure, the kit comprising:

a plurality of substantially rigid discrete support segments for disposition at least partially circumferentially about the anatomical structure to form a line of discrete support segments;

each segment including a plurality of suture apertures constructed to receive and support suture material for attaching each segment in fixed relationship with respect to the anatomical structure at a precise location, the suture apertures being spaced such that suture material passing through the suture apertures creates a plication region in the anatomical structure beneath each segment, the line of segments being disposed to create a series of plication regions in the anatomical structure to reduce the circumference of the anatomical structure by a precise amount along the line of segments.

22. An anatomical structure circumference reduction apparatus for precisely reducing the circumference of an anatomical structure, the apparatus comprising:

a plurality of substantially rigid discrete support segments for disposition at least partially circumferentially about the anatomical structure to form a line of discrete support segments; each segment including a plurality of suture apertures constructed to receive and support suture material for attaching each segment with respect to the anatomical structure at a precise location, the apertures of each segment and the line of segments being constructed and arranged to create a plication region in the anatomical structure beneath each segment and to create a series of plication regions in the anatomical structure to reduce the circumference of the anatomical structure by a precise amount along the line of segments; and stabilizing material for covering the line of segments to stabilize the line of segments and to substantially prevent contact of the line of segments with blood.

23. A vascular structure circumference reduction apparatus for precisely reducing the circumference of a vascular structure, the apparatus comprising:

circumference reduction means for creating a series of plication regions in the vascular structure, the circumference reduction means comprising a plurality of substantially rigid discrete support segments for disposition at least partially circumferentially about the vascular structure to form a line of discrete support segments, each plication region in the series of plication regions being disposed beneath each segment, and to reduce the circumference of the vascular structure along the circumference reduction means by a precise amount, each segment of the circumference reduction means including aperture means for receiving and supporting suture means for attaching each segment to the vascular structure at a precise location, the circumference reduction means providing flexibility to follow the vascular structure while substantially preventing circumferential lengthening of the vascular structure; and stabilizing means for covering the line of segments and for stabilizing the line of segments and substantially preventing contact of the line of segments with blood.

* * * * *